(12) United States Patent
Abdel Maksoud et al.

(10) Patent No.: US 8,987,199 B2
(45) Date of Patent: Mar. 24, 2015

(54) PHARMACEUTICAL COMPOSITIONS FOR INTRANASAL ADMINISTRATION FOR THE TREATMENT OF NEURODEGENERATIVE DISORDERS

(75) Inventors: Yaser A. Abdel Maksoud, Oak Lawn, IL (US); Mustafa A. Maher, Phoenix, AZ (US)

(73) Assignee: Nerve Access, Inc., Chicago Ridge, IL (US)

( * ) Notice: Subject to any disclaimer, the term of this patent is extended or adjusted under 35 U.S.C. 154(b) by 0 days.

(21) Appl. No.: 13/525,176

(22) Filed: Jun. 15, 2012

(65) Prior Publication Data

US 2012/0322727 A1    Dec. 20, 2012

Related U.S. Application Data

(60) Provisional application No. 61/497,188, filed on Jun. 15, 2011.

(51) Int. Cl.
| | | |
|---|---|---|
| A61P 25/28 | (2006.01) |
| A61P 25/00 | (2006.01) |
| A61K 9/12 | (2006.01) |
| A61K 9/10 | (2006.01) |
| A61K 9/08 | (2006.01) |
| A61K 38/28 | (2006.01) |
| A61K 31/47 | (2006.01) |
| A61K 9/00 | (2006.01) |
| A61K 47/10 | (2006.01) |
| A61K 47/20 | (2006.01) |

(52) U.S. Cl.
CPC ............. *A61K 31/47* (2013.01); *A61K 38/28* (2013.01); *A61K 9/0048* (2013.01); *A61K 47/10* (2013.01); *A61K 47/20* (2013.01); *A61K 9/08* (2013.01)
USPC ........................ 514/6.5; 514/17.7; 514/17.8

(58) Field of Classification Search
CPC ....... A61K 31/47; A61K 47/00; A61K 47/06; A61K 47/10; A61K 47/20; A61K 9/0043; A61K 9/08; A61K 38/28; A61K 38/00; A61K 38/22; A61K 2300/00
USPC ........................................................ 514/6.5
See application file for complete search history.

(56) References Cited

U.S. PATENT DOCUMENTS

| | | | |
|---|---|---|---|
| 3,551,554 A * | 12/1970 | Herschler | .......... 424/9.4 |
| 5,624,898 A | 4/1997 | Frey, II | |
| 6,180,603 B1 | 1/2001 | Frey, II | |
| 6,313,093 B1 | 11/2001 | Frey, II | |
| 6,342,478 B1 | 1/2002 | Frey, II | |
| 6,407,061 B1 | 6/2002 | Frey, II | |
| 6,991,785 B2 | 1/2006 | Frey, II | |
| 7,084,126 B1 | 8/2006 | Frey, II et al. | |
| 7,273,618 B2 | 9/2007 | Frey, II | |
| 7,618,615 B2 | 11/2009 | Frey, II et al. | |
| 7,731,947 B2 | 6/2010 | Eliaz | |
| 7,776,312 B2 | 8/2010 | Frey, II et al. | |
| 7,989,502 B2 | 8/2011 | Greco et al. | |
| 2002/0072498 A1 | 6/2002 | Frey, II | |
| 2002/0082215 A1 | 6/2002 | Frey, II | |
| 2002/0169102 A1 | 11/2002 | Frey, II | |
| 2003/0072793 A1 | 4/2003 | Frey, II et al. | |
| 2005/0031651 A1 * | 2/2005 | Gervais et al. | ............. 424/400 |
| 2005/0191245 A1 * | 9/2005 | Adams et al. | ............. 424/45 |
| 2006/0074104 A1 | 4/2006 | Bush | |
| 2007/0020196 A1 | 1/2007 | Pipkin | |
| 2007/0054843 A1 | 3/2007 | Yeomans et al. | |
| 2007/0092500 A1 | 4/2007 | Frey, II et al. | |
| 2007/0093420 A1 | 4/2007 | Yeomans et al. | |
| 2008/0248099 A1 | 10/2008 | Ishii | |
| 2009/0233912 A1 * | 9/2009 | Castile et al. | ............. 514/220 |
| 2009/0264506 A1 | 10/2009 | Reinhard et al. | |
| 2009/0325860 A1 * | 12/2009 | Costantino et al. | ............. 514/3 |
| 2009/0325917 A1 * | 12/2009 | Lulla et al. | ............. 514/172 |

FOREIGN PATENT DOCUMENTS

| | | |
|---|---|---|
| WO | 91/07947 | 6/1991 |
| WO | 00/33813 | 12/1999 |
| WO | 00/33814 | 6/2000 |
| WO | 01/41782 A2 | 6/2001 |

(Continued)

OTHER PUBLICATIONS

Born et al., Nature Neuroscience (2002) vol. 5, No. 6, 514-516.*
Rowe, Raymond C; Sheskey, Paul J; Quinn, Marian E. Handbook of Pharmaceutical Excipients [e-book]. Pharmaceutical Press; 2009 [cited Jan. 16, 2013]. Available from: MyiLibrary. <http://lib.myilibrary.com?ID=231717>.*
Pires et al., Jharm Pharmacert Sci (www.cspsCanada.org) (2009) 12(3). 288-311.*
PCT, Notification of Transmittal of the International Search Report and the Written Opinion of the International Searching Authority, or the Declaration, in International application No. PCT/US12/42819, dated Oct. 1, 2012. (23 pages).

(Continued)

*Primary Examiner* — Karlheinz R Skowronek
*Assistant Examiner* — Catherine Mader
(74) *Attorney, Agent, or Firm* — McAndrews Held & Malloy, Ltd.

(57) ABSTRACT

In one embodiment of the invention, a pharmaceutical composition for intranasal administration comprises insulin, dimethyl sulfoxide and at least one pharmaceutically acceptable excipient. In another embodiment of the invention, a pharmaceutical composition for intranasal administration comprises clioquinol, dimethyl sulfoxide and at least one pharmaceutically acceptable excipient. In yet another embodiment of the invention, a pharmaceutical composition for intranasal administration comprises insulin, clioquinol, dimethyl sulfoxide and at least one pharmaceutically acceptable excipient. The pharmaceutical compositions of the invention may be used to treat or prevent a neurodegenerative disorder such as Alzheimer's disease, stroke, Parkinson's disease, multiple sclerosis, spinal cord injuries, and/or traumatic brain injuries and the like, in addition to other systemic and local diseases.

3 Claims, 6 Drawing Sheets

(56) References Cited

FOREIGN PATENT DOCUMENTS

| WO | 02/32449 A2 | 4/2002 |
|---|---|---|
| WO | 02/86105 A1 | 4/2002 |
| WO | 03/072056 | 9/2003 |

OTHER PUBLICATIONS

PCT, Notification Concerning Transmittal of International Preliminary Report on Patentability, in Application No. PCT/US2012/042819, dated Jan. 3, 2014. (9 pages).
Ritchie, Craig W., et al.: Metal-Protein Attenuation With Iodochlorhydroxyquin (Clioquinol) Targeting Aβ Amyloid Deposition and Toxicity in Alzheimer Disease. Arch Neurol/vol. 60, Dec. 2003, p. 1685-1691.
Banks, William A., et al.: Brain Uptake of the Glucagon-Like Peptide-1 Antagonist Exendin(9-39) after Internasal Administration. The Journal of Pharmacology and Experimental Therapies, vol. 309, No. 2, p. 469-475, 2003.
Craft Suzanne, et al., Insulin and neurodegenerative disease: shared and specific mechanisms. The Lancet Neurology, vol. 3, Mar. 2004, p. 169-178.
Craft, Suzanne, et al., Intranasal Insulin Therapy for Alzheimer Disease and Amnestic Mild Cognitive Impairment. Arch Neurol. Published online Sep. 12, 2011. doi:10.1001/archneurol.2011.233.
De Felice, Fernanda G., et al., Protection of synapses against Alzehimer's-linked toxins: Insulin signaling prevents the pathogenic binding of Aβ oligomers. PNAS, Feb. 10, 2009, vol. 106, No. 6, p. 1971-1976.
Bareggi, Silvio R., et al., Clioquinol: Review of its Mechanisms of Action and Clinical Uses in Neurodegenerative Disorders. CNS Neuroscience & Therapeutics 00 (2010) 1-6, Blackwell Publishing Ltd.
Regland, Björn, et al., Treatment of Alzheimer's Disease with Clioquinol, Original Research Article, Dement Geriat Cogn Disord 2001;12:408-414, accepted Jun. 20, 2001.
Reger, M.A., et al., Intranasal insulin improves cognition and modulates β-amyloid in early AD. Neurology 70, Feb. 5, 2008, Epub Oct. 17, 2007. Erratum in: Neurology; 70(6):440-8.
Dhamoon M.S., et al., Intranasal insulin improves cognition and modulates beta-amyloid in early AD. Neurology; 72(3):292-3; 2009; PMID: 19153380.
Craft, Suzanne, Insulin resistance and Alzheimer's disease pathogenesis: potential mechanisms and implication for treatment. Curr Alzheimer Res; 4(2): 147-52. Review. 2007.
Grossi, C., et al., Clioquinol decreases amyloid-beta burden and reduces working memory impairment in a transgenic mouse model of Alzeimer's disease. J. Alzeimers Dis.; 17(2):423-40. 2009.
Hanson, L.R., et al, Intranasal delivery by passes the blood-brain barrier to target therapeutic agents to the central nervous system and treat neurodegenerative disease. BMC Neurosci. 10;9 Suppl. 3:S5. Review. 2008.
Skoog (2000) N. Eng. J. Med. 343:502-503.
Bush, Asley I., Metal complexing agents as therapies for Alzheimer's disease. Neurobiology of Aging 23 (2002) p. 1031-38.
Dhuria, Shyeilla V., et al., Intranasal Delivery to the Central Nervous System: Mechanisms and Experimental Considerations. Journal of Pharmaceutical Sciences, vol. 99, No. 4, Apr. 2010.
Dhanda, Devender S., et al., Approaches from Drug Deposition in the Human Olfactory Epithelium. Drug Delivery Technology, Apr. 2005, vol. 5, No. 4 p. 64-72.
Frey, William H., Ph.D., Bypassing the Blood-Brain Barrier to Deliver Therapeutic Agents to the Brain and Spinal Cord. Drug Delivery Technology, http://www.drugdeliverytech.com/gii-bin/articles.cgi?id.Article=62 (Jul. 17, 2007).
Finefrock, Anne E., et al., Current Status of Metals as Therapeutic Targets in Alzheimer's Disease. JAGS 51:1143-1148, 2003 American Geriatrics Society.

* cited by examiner

PHARMACEUTICAL COMPOSITIONS FOR INTRANASAL ADMINISTRATION FOR THE TREATMENT OF NEURODEGENERATIVE DISORDERS

FIELD OF THE INVENTION

The invention relates to pharmaceutical compositions for the treatment or prevention of neurodegenerative disorders. More specifically, the invention relates to (1) a pharmaceutical composition for intranasal administration comprising insulin and dimethyl sulfoxide, (2) a pharmaceutical composition for intranasal administration comprising clioquinol and dimethyl sulfoxide, and (3) a pharmaceutical composition for intranasal administration comprising insulin, clioquinol and dimethyl sulfoxide. The pharmaceutical compositions of the invention may be used to treat or prevent a neurodegenerative disorder such as Alzheimer's disease, stroke, Parkinson's disease, multiple sclerosis, spinal cord injuries, and traumatic brain injuries.

BACKGROUND

Neuroscientists and other experts in the field have long held that regenerating the cells and tissues of the central nervous system (CNS) following a neurological injury was not possible. However, recent research has confirmed that certain cellular and molecular compounds, as well as tissue conduits, may be used to improve functional recovery after onset of a neurodegenerative disorder, such as Alzheimer's disease (AD), stroke, Parkinson's disease (PD), multiple sclerosis (MS), spinal cord injuries (SCI), and traumatic brain injuries (TBI).

Alzheimer's disease is a chronic, degenerative and terminal neurological disorder with a number of factors influencing its development and manifestations. About 5.4 million Americans and 36 million worldwide suffer from Alzheimer's, a number which is expected to increase dramatically. Every 68 seconds a new individual develops Alzheimer's in the USA only. An average Alzheimer's patient spends $2,400/year on therapeutics. Direct and indirect costs of Alzheimer's and other dementias in the USA are more than $170 billion and $400 billion worldwide annually. Thus, developing a drug that reverses the pathology of Alzheimer's will significantly reduce these costs.

Minor pathological changes may appear in patients decades before clinical symptoms of Alzheimer's disease occur, and they may be found in middle-aged and elderly persons without obvious symptoms of AD. The preclinical stage of Alzheimer's disease (i.e., preclinical Alzheimer's disease) is characterized by mild impairment in verbal memory, which probably reflects damage to the hippocampus, with later involvement of areas governing language, spatial orientation, attention, concentration, and psychomotor speed. See Skoog (2000) N. Eng. J. Med. 343:502-503, incorporated herein by reference.

Several animal and human efficacy studies have confirmed that therapeutics including macromolecules and even stem cells can reach the brain and upper spinal cord through the roof of the nose directly, without having to access the blood stream or pass through the blood brain barrier (BBB) as they travel along the olfactory and trigeminal pathways and nerve fibers. Human studies have indicated that intranasally delivered insulin decreases the cognitive decline associated with Alzheimer's. Experts in the field have highlighted ten different mechanisms through which intranasal insulin significantly enhances cognition in AD and other neurodegenerative diseases, including reduction in amyloid plaque synthesis with enhanced breakdown, elevation of acetylcholine brain levels, enhanced neurogenesis and synaptogenesis, increased glucose uptake by brain cells with enhanced oxidative phosphorylation and energy metabolism. See, for example, Dhamoon et al. (2009) "Intranasal insulin improves cognition and modulates beta-amyloid in early AD" *Neurology* 72(3): 292-3; Reger et al. (2008) "Intranasal insulin improves cognition and modulates beta-amyloid in early AD" *Neurology* 70(6):440-8; Craft (2007) "Insulin resistance and Alzheimer's disease pathogenesis: potential mechanisms and implications for treatment" *Curr. Alzheimer Res.* 4(2):147-52; Grossi et al. (2009) "Clioquinol decreases amyloid-beta burden and reduces working memory impairment in a transgenic mouse model of Alzheimer's disease" *J. Alzheimers Dis.* 17(2):423-40; and Hanson et al. (2008) "Intranasal delivery bypasses the blood-brain barrier to target therapeutic agents to the central nervous system and treat neurodegenerative disease" *BMC Neurosci.* 10; 9 Suppl 3:S5., each of which is incorporated herein by reference.

Although therapies for Alzheimer's disease and other neurodegenerative disorders exist, additional treatment options are needed. For instance, currently-approved Alzheimer's drugs are symptomatic and may be used for 24 months at most; they are not effective and cannot slow down or reverse the disease.

SUMMARY OF THE INVENTION

In one embodiment, the invention is a pharmaceutical composition for intranasal administration, comprising an effective amount of insulin, dimethyl sulfoxide, and a pharmaceutically acceptable excipient. In another embodiment, the invention is a pharmaceutical composition for intranasal administration, comprising: insulin present in an amount from about 400 IU/mL to about 600 IU/mL; dimethyl sulfoxide present in an amount from about 24% (v/v) to about 36% (v/v); polyethylene glycol present in an amount from about 1.6% (v/v) to about 2.4% (v/v); glycerin present in an amount from about 1.2% (v/v) to about 1.8% (v/v); and phenol present in an amount from about 0.05% (v/v) to about 0.15% (v/v). In a further embodiment, the invention is a pharmaceutical composition for intranasal administration, comprising about 500 IU/mL insulin, about 30% (v/v) dimethyl sulfoxide, about 2% (v/v) polyethylene glycol, about 1.5% (v/v) glycerin, and about 0.1% (v/v) phenol.

In another embodiment, the invention is a pharmaceutical composition for intranasal administration, comprising an effective amount of clioquinol, dimethyl sulfoxide, and a pharmaceutically acceptable excipient. In another embodiment, the invention is a pharmaceutical composition for intranasal administration, comprising: clioquinol present in an amount from about 2.4% (w/v) to about 3.6% (w/v); dimethyl sulfoxide present in an amount from about 34% (v/v) to about 52% (v/v); polyethylene glycol present in an amount from about 5.4% (v/v) to about 8.0% (v/v); propylene glycol present in an amount from about 5.4% (v/v) to about 8.0% (v/v); glycerin present in an amount from about 21% (v/v) to about 33% (v/v); boric acid present in an amount from about 0.13% (w/v) to about 0.21% (w/v); and sodium bicarbonate present in an amount from about 0.24% (w/v) to about 0.36% (w/v). In a further embodiment, the invention is a pharmaceutical composition for intranasal administration, comprising about 3% (w/v) clioquinol, about 43% (v/v) dimethyl sulfoxide, about 6.7% (v/v) polyethylene glycol, about 6.7% (v/v) propylene glycol, about 27% (v/v) glycerin, about 0.17% (w/v) boric acid, and about 0.3% (w/v) sodium bicarbonate.

In yet another embodiment, the invention is a pharmaceutical composition for intranasal administration, comprising an effective amount of insulin, clioquinol, dimethyl sulfoxide, and a pharmaceutically acceptable excipient. In another embodiment, the invention is a pharmaceutical composition for intranasal administration, comprising: insulin present in an amount from about 400 IU/mL to about 600 IU/mL; clioquinol present in an amount from about 2.4% (w/v) to about 3.6% (w/v); dimethyl sulfoxide present in an amount from about 34% (v/v) to about 52% (v/v); polyethylene glycol present in an amount from about 5.4% (v/v) to about 8.0% (v/v); propylene glycol present in an amount from about 5.4% (v/v) to about 8.0% (v/v); glycerin present in an amount from about 21% (v/v) to about 33% (v/v); phenol present in an amount form about 0.05% (v/v) to about 0.15% (v/v); boric acid present in an amount from about 0.13% (w/v) to about 0.21% (w/v); and sodium bicarbonate present in an amount from about 0.24% (w/v) to about 0.36% (w/v). In a further embodiment, the invention is a pharmaceutical composition for intranasal administration comprising about 500 IU/mL insulin, about 3% (w/v) clioquinol, about 43% (v/v) dimethyl sulfoxide, about 6.7% (v/v) polyethylene glycol, about 6.7% (v/v) propylene glycol, about 27% (v/v) glycerin, about 0.1% (v/v) phenol, about 0.17% (w/v) boric acid, and about 0.3% (w/v) sodium bicarbonate.

In additional embodiments, the invention is a method of treating, preventing, or reversing cognitive decline in a patient having clinical or pre-clinical Alzheimer's disease, comprising intranasally administering an effective amount of one of the foregoing compositions of the invention. In yet another embodiment, the invention is a method of improving cognition in a patient having clinical or pre-clinical Alzheimer's disease, comprising intranasally administering an effective amount of a composition of the invention. In a further embodiment, the invention is a method of improving memory retention in a patient having clinical or pre-clinical Alzheimer's disease, comprising intranasally administering an effective amount of a composition of the invention. In a still further embodiment, the invention is a method of treating a neurodegenerative disorder in a patient comprising intranasally administering a composition of the invention.

DETAILED DESCRIPTION OF THE INVENTION

The pharmaceutical compositions of the invention are formulated to be administered intranasally. An intranasal route of administration allows the pharmaceutical composition to travel through the roof of the nose. The pharmaceutical compositions can travel directly to the central nervous system (CNS) without having to cross the blood brain barrier or access the blood stream. The pharmaceutical compositions travel from the roof of the nose along the fibers of the olfactory and trigeminal nerves (Cranial Nerves I & V), found in the mucosa of the nose, to the extracellular space of the neurons of the brain and spinal cord. Therefore, the rest of the body's organs are not exposed to the drug, reducing its side effects and required dosage.

Intranasal administration of the pharmaceutical compositions of the invention delivers the pharmaceutical compositions directly to the brain and spinal cord. This method does not target the lungs (like inhalational products for bronchial asthma). This method also does not target the nose locally (like antiallergics). Nor does this method target the blood stream in the nasal mucosa. Intranasal administration of the present pharmaceutical compositions does not reach the blood stream or only reaches it minimally. Rather, the pharmaceutical compositions of the invention reach the brain and spinal cord along the olfactory and trigeminal fibers traveling through the roof of the nose.

Intranasal drug delivery offers an improved method to treat Alzheimer's disease and other neurodegenerative disorders. Invasive methods of drug administration are often not practical when used in humans due to issues with inconvenience, customer compliance, safety, and cost. On the other hand, intranasal drug delivery provides a non-invasive and practical method of delivering therapeutic agents directly to the central nervous system including the brain and spinal cord. The blood brain barrier restricts the use of numerous therapeutic agents and limits their central nervous system penetration depending on molecular size and charge. Direct nose-to-brain drug delivery circumvents the possible risks associated with their oral, rectal, parenteral or pulmonary administration and the side effects that may accompany the systemic exposure to these pharmaceutics. Therapeutics, including both small molecules and macromolecules (like insulin), may be targeted and delivered rapidly and directly to the central nervous system because of the unique connections that the olfactory and trigeminal nerve fibers provide between the central nervous system and the nasal cavity.

The pharmaceutical compositions of the invention may be liquid, e.g. adapted for administration as a spray. Liquid preparations, such as those based on aqueous formulations, will usually include ancillary agents, for example a pH-buffering system, preferably a buffer such as phosphate, borate, citrate or acetate buffers, a preservative and an osmotic pressure controlling agent, e.g. glycerol or sodium chloride. For instance, boric acid, sodium bicarbonate, sodium phosphate monobasic, sodium phosphate dibasic, and sodium phosphate dibasic heptahydrate may be used as buffering agents. Furthermore, boric acid and sodium bicarbonate may be used together in a buffer system; sodium phosphate monobasic and sodium phosphate dibasic may be used together in a buffer system; and sodium phosphate dibasic heptahydrate may be used in a buffer system.

Preferred liquid preparations are those in which the diluent is water. Such preparations may be prepared by dispersing the pharmaceutically active agent and ancillary agents, the dispersion being conducted by any method usually employed for suspension or emulsification, e.g. ultrasonic treatment. Adjustment of the aqueous phase to neutrality (i.e. to pH in the range from about 6.5 to about 8) may be accomplished in any of the preparatory steps. Preferably, microemulsions are prepared in which the size of the dispersed particles or droplets is of the order of 10 nm, thereby facilitating their passage across the nasal mucosa. Such microemulsions may be sterilized by filtration.

Pharmaceutically acceptable excipients, including dispersing agents, isotonicity agents, stabilizing agents and the like are used as appropriate in the pharmaceutical compositions of the invention. *Remington's Pharmaceutical Sciences*, Mack Publishing Co., Easton, Pa., latest edition, incorporated herein by reference, provides a compendium of formulation techniques as are generally known to practitioners. The *Handbook of Pharmaceutical Excipients*, Pharmaceutical Press, Grayslake, Ill., latest edition, incorporated herein by reference, provides a compendium of pharmaceutically acceptable excipients that may be used in the pharmaceutical compositions of the invention.

The pharmaceutical compositions of the invention may contain excipients such as, for example, antioxidants, chemical preservatives, buffering agents, agents that increase viscosity, diluents, pH adjusters, and solvents.

Antioxidants are substances that prevent oxidation of the formulations. Suitable antioxidants for use in the compositions of the invention include, but are not limited to, butylated hydroxytoluene, butylated hydroxyanisole, potassium metabisulfite, and the like.

In some embodiments of the invention, the composition contains a preservative that is chosen in quantities that preserve the composition, but do not cause irritation of the nasal mucosa. Suitable preservatives for use in some embodiments of the compositions of the invention include, but are not limited to, benzalkonium chloride, methyl, ethyl, propyl or butylparaben, benzyl alcohol, phenylethyl alcohol, benzethonium, or combination thereof.

If a buffering agent is employed in the composition, it is chosen in quantities that preferably do not irritate the nasal mucosa. Buffering agents include agents that reduce pH changes. Preferred buffering agents for use in the present invention include, but are not limited to, salts of borate, citrate, acetate, or phosphate. The most preferred buffers include boric acid and sodium bicarbonate, sodium phosphate heptahydrate, sodium phosphate monobasic and sodium phosphate dibasic, sodium citrate, sodium acetate, potassium dihydrogen phosphate, and a citrate buffer comprising sodium citrate and citric acid.

The pharmaceutical compositions of the invention may include one or more agents that increase viscosity chosen in quantities that preferably do not irritate the nasal mucosa and increase nasal retention time. Preferred agents that increase viscosity include, but are not limited to, methylcellulose, carboxymethylcellulose sodium, ethylcellulose, carrageenan, carbopol, and/or combinations thereof.

Suitable diluents include aqueous or non-aqueous diluents or combination thereof. Examples of aqueous diluents include, but are not limited to, saline, water, dextrose or combinations thereof. Non-aqueous diluents include, but are not limited to, alcohols, particularly polyhydroxy alcohols such as propylene glycol, polyethylene glycol, glycerol, and vegetable and mineral oils. These aqueous and/or non-aqueous diluents can be added in various concentrations and combinations to form solutions, suspensions, oil-in-water emulsions or water-in-oil emulsions.

The pH of the compositions of the invention may be adjusted to the desired value using any suitable organic or inorganic acid or organic or inorganic base. Suitable organic acids include, but are not limited to, acetic acid, citric acid, glutamic acid and methane sulfonic acid. Suitable inorganic acids include, but are not limited to, hydrochloric acid and sulphuric acid. Suitable organic bases include, but are not limited to, meglumine, lysine and tromethamine (TRIS). Suitable inorganic bases include, but are not limited to, sodium hydroxide and potassium hydroxide.

Solvents that may be used to prepare the compositions of the invention include, but are not limited to, water, ethanol, propylene glycol, polyethylene glycol, glycerin, phenol, glycofurol, benzyl benzoate and polyoxyethylene castor oil derivatives.

The pharmaceutical compositions of the invention may contain other pharmaceutically acceptable ingredients well known in the art. Such excipients include, but are not limited to, chelating agents (such as edetic acid or one of its salts), flavors, sweeteners, thickening, adhesive or gelling agents, including, but not limited to, celluloses such as hydroxypropyl methylcellulose, methylcellulose, hydroxypropyl cellulose, sodium carboxyl cellulose and microcrystalline cellulose, poloxomers, polyethylene glycols, carbomers or polyethylene oxide.

The concentration of the pharmaceutically active agent in the preparations of this invention will depend on the particular agent chosen, on its efficacy, on a comparison of its bioavailability by nasal administration and by other routes of administration, for example parenteral injection, and on the desired frequency of administration combined with the desired single dosage of the formulation. Such pharmacological data can routinely be obtained by the skilled artisan from animal experiments, for example in terms of index values.

The pharmaceutical compositions of the invention may be used in any dosage dispensing device adapted for intranasal administration. The device should be constructed with a view to ascertaining optimum metering accuracy and compatibility of its constructive elements. The compositions may be administered as drops, sprays, aerosols or by any other intranasal dosage form. Optionally, the delivery system may be a unit dose delivery system. The volume of solution or suspension delivered per dose may be anywhere from 10 to 1000 uL and preferably between 50 and 300 uL. Delivery systems for these various dosage forms may be dropper bottles, plastic squeeze units, atomizers, nebulizers, metered nasal sprayers, or pharmaceutical aerosols in either unit dose or multiple dose packages. Aerosol systems require a propellant to be inert towards the formulation. Suitable propellants may be selected among such gases as fluorocarbons, hydrocarbons, nitrogen and dinitrogen oxide or mixtures thereof.

A preferred method of administering the solutions of the invention is using a spray device. Spray devices can be single ("unit") dose or multiple dose systems, for example comprising a bottle, pump and actuator, and are available from various commercial sources.

For a spray device, the typical volume of liquid that is dispensed in a single spray actuation is from 0.01 to 0.14 ml, for example from 0.05 to 0.14 ml, such as 0.1 ml. It is a practical proposition to administer up to about 0.2 ml into each nostril (i.e. two.times.0.1 ml sprays) to provide a therapeutic dose of drug, although the most acceptable dosing regimen would be one spray into one or both nostrils.

The invention also provides a nasal drug delivery device or a dose cartridge for use in a nasal delivery device loaded with a composition of the invention.

In certain embodiments, a pharmaceutical composition of the invention comprises insulin, dimethyl sulfoxide, and a pharmaceutically acceptable excipient, wherein the composition is formulated for intranasal administration.

In certain embodiments, a pharmaceutical composition of the invention comprises clioquinol, dimethyl sulfoxide, and a pharmaceutically acceptable excipient, wherein the composition is formulated for intranasal administration.

In certain embodiments, a pharmaceutical composition of the invention comprises insulin, clioquinol, dimethyl sulfoxide, and a pharmaceutically acceptable excipient, wherein the composition is formulated for intranasal administration.

Insulin is a protein hormone consisting of an amino acid sequence isolated from the pancreas where it exists in crystalline form. The crystallization of insulin requires zinc which is stored in the pancreatic tissue that is relatively rich in this element. The insulin molecule consists of two chains connected by two disulfide bridges. Alkali, reducing agents, or digestive enzymes break the disulfide bonds and inactivates the insulin. The crystal structure has several alpha helical ($\alpha$-helix) regions in the chains. In solution, insulin can exist as a monomer, dimer, or as a hexamer in the presence of zinc. Two molecules of $Zn^{2+}$ are coordinated in the hexamer, and this form of insulin is stored in the pancreatic beta-cells ($\beta$-cells).

Insulin is hexameric in the highly concentrated preparations of crystalline insulin solution used for therapy and after absorption, the concentration of insulin falls to physiological levels and the hormone dissociates into monomers, which is the biologically active form of insulin. Studies suggest that low levels of insulin in the brain or reduced insulin signaling (insulin resistance) is associated with the increased risk of AD and altered CNS function due to reduction or down-regulation of insulin transport to the brain and the formation of $\beta$-amyloid peptide (AB) which is an essential ingredient of the senile plaque; the more aggregation of this peptide the higher is the neurotoxicity.

Insulin has various memory-related physiological and pharmacological actions. For instance, insulin increases the uptake and metabolism of glucose by brain cells, thus enhancing the oxidative metabolism and ATP production by neurons. Augmenting the oxidative phosphorylation inside neurons prevents abnormally high intraneuronal acidosis; increased acidosis is known to enhance the formation of $\beta$-Amyloid ($A\beta$) inside neurons. In addition, Insulin seems to modulate long-term potentiation through influencing brain cell expression of NMDA receptors. Insulin also increases the levels of some CNS neurotransmitters such as acetylcholine and norepinephrine which modulate the cerebral blood flow and cognitive power of the brain. Furthermore, insulin increases the level of Insulin degrading enzyme (IDE) in brain tissues. IDE is a $Zn^{2+}$ metalloprotease that degrades $A\beta$ and plays a crucial role in its clearance in the brain.

Additionally, Insulin has been shown to enhance the release of $A\beta$ from the intracellular to the extracellular compartment of neurons for clearance outside the cell. Insulin inhibits hyperphosphorylation of tau which is an important step of the formation of the neurofibrillary tangles inside neurons; one of the main hallmarks of the pathology of AD. Inflammation has been found to be a critical promoter of AD. Insulin has anti-inflammatory effects that can counteract the inflammatory reactions leading to AD. Moreover, Insulin has been found to downregulate the binding sites of the soluble amyloid beta oligomers (also referred to as $A\beta$-derived diffusible ligands "ADDLs"). The latter act as pathogenic ligands whose binding to specific synapses in the brain lead to a) inhibition of long-term potentiation, b) enhanced tau hyperphosphorylation, c) oxidative stress, and d) synapse and synaptic spine deterioration and loss. Furthermore, insulin enhances the hippocampal inhibition of the hypothalamic-pituitary-adrenal axis leading to reduction in the glucocorticoid production by the adrenals. Consequently, insulin reverses the effects of glucocorticoids on the pathophysiology of AD that include: a) enhancing production of $A\beta$, b) reducing amyloid degradation, c) facilitating plaque formation, d) enhancing $A\beta$-mediated neuronal toxicity, and e) increasing tau formation.

In certain embodiments, the insulin in a pharmaceutical composition of the invention is human recombinant insulin. The insulin may be provided in the present pharmaceutical composition at a dose per volume of from 0 to 200 IU/ml, 100 to 300 IU/ml, 300 to 500 IU/ml, or 500 IU/ml to 1000 IU/ml, which will provide 0-20 IU/0.1 ml, 10-30 IU/0.1 ml, 30-50 IU/0.1 ml, and 50-100 IU/0.1 ml, respectively, as needed. Preferably, the insulin may be provided in the present pharmaceutical composition at a dose per volume of from 50 to 150 IU/ml, 150 to 250 IU/ml, and 350 to 450 IU/ml which will provide 5-15 IU/0.1 ml, 15-25 IU/0.1 ml, and 35-45 IU/0.1 ml respectively as needed. Preferably, the insulin may be provided in the present pharmaceutical composition at a dose per volume of about 100 IU/ml, about 200 IU/ml, about 400 IU/ml, or about 500 IU/ml, which will provide about 10 IU/0.1 ml, about 20 IU/0.1 ml, about 40 IU/0.1 ml, and about 50 IU/0.1 ml, respectively, as needed. A therapeutic dose for the recombinant insulin is approximately 20-40 IU/day. A suitable dose range for recombinant insulin is approximately 10-80 IU/day. Also disclosed is a formulation containing a toxic dose of insulin (500 IU/day) used for animal toxicity studies.

In certain embodiments, a pharmaceutical composition of the invention also comprises dimethyl sulfoxide (DMSO). DMSO has been identified as an absorption enhancer and therapy potentiating agent in the treatment of neurological disorders such as AD. DMSO has the empirical formula ($C_2H_6OS$). DMSO is an organic solvent. It is a polar aprotic organo-sulfur compound. Its dissociable hydrogen atom may be donated to an oxygen atom and it does not exchange protons with a substance dissolved in it. DMSO dissolves both polar and nonpolar compounds and it is miscible with a wide range of organic solvents as well as with water. Polar protic solvents are compounds that share ion dissolving power with aprotic solvents, but have acidic hydrogen. These solvents generally have high polarity and can interact through dipole-dipole intermolecular forces and hydrogen bonding.

Amyloid plaque formation plays a role in a wide range of human diseases including AD. The degree of peptide aggregation has been associated with the severity of neurotoxicity and the level of dementia. DMSO has an inhibitory effect on the growth of beta-sheets by altering its biological activity, and through its solubilizing effects on the self-assembled beta-amyloid peptides. DMSO disrupts the formation of secondary structures of native insulin and insulin fibrils. Aqueous solutions of DMSO solubelize insulin fibrils while maintaining their $\beta$-pleated structure.

DMSO offers numerous advantages in the present composition. DMSO (dimethyl sulfoxide) is not used in the present composition as a symptomatic treatment but as a disease-modifying therapeutic, i.e. DMSO reverses the pathology of AD. DMSO stabilizes insulin in the formula. DMSO significantly potentiates the effect of insulin. DMSO helps the absorption of insulin through the roof of the nose (absorption enhancer). DMSO itself has a therapeutic effect against the pathology of AD.

Dimethyl sulfoxide may be present in an amount from about 10 to about 50% (v/v), preferably from about 20% to about 40% (v/v), and more preferably about 24% to about 36% (v/v).

In certain embodiments, a pharmaceutical composition of the invention comprises polyethylene glycol (PEG). PEG is a member of the Glycols which are dihydroxy alcohols; they have more than one site of hydrogen bonding. Glycols have higher water solubility than the single hydroxy alcohols, for example, ethyl alcohol. PEG is a polymer of ethylene oxide and water. PEG 400 is used in pharmaceutical formulations as a solvent vehicle for formulating products intended for internal and external use. It is a clear, colorless, slightly hygroscopic, viscous liquid with a slight odor. PEG is miscible with glycerin and DMSO, and compatible with phenol. Polyethylene glycol may be present in an amount from about 1-3% (v/v), preferably from about 1.6% to about 2.4% (v/v).

In certain embodiments, a pharmaceutical composition of the invention comprises glycerin. Glycerin is a member of the Glycols. It is soluble in water, PEG and DMSO. It is used as a solvent vehicle in internal, external and parenteral pharmaceutical formulations. Glycerin may be present in an amount from about 1-3% (v/v), preferably from about 1.2-1.8% (v/v).

In certain embodiments, a pharmaceutical composition of the invention comprises phenol. Phenol is also known as carbolic acid with the chemical formula $C_6H_5OH$. Phenol is an organic compound that is soluble in water and miscible with glycerin and DMSO and is compatible with all other ingredients of the present composition. Phenol is used as a stabilizer and preservative in insulin formulations. The structures of insulin in the related rhombohedral crystals show two $Zn^{2+}$-insulin and four $Zn^{2+}$-insulin hexamer molecules organized as three dimmers, and that phenol molecules found bonding specifically to each molecule and stabilizes this new helical conformation. Phenol may be present in an amount from about 0.1 to about 4.0%, preferably about 0.2-0.3% or about 2.0-3.0% (v/v).

The use of co-solvents such as glycerol, polyethylene glycol and ethanol in pharmaceutical compositions used for intranasal application may increase active ingredient absorption; they are non-toxic, pharmaceutically accepted and non-irritant to nasal mucosa. Due to the small size of the nasal cavity, the volume of active ingredient solution allowed for intranasal administration is small, and these co-solvents allow for sufficient active ingredient in solution.

In certain embodiments, zinc chloride is added to the insulin powder of a pharmaceutical composition to produce a stable hexamer which may be solubilized in an aqueous solvent maximizing the solubilization and stabilization of the composition. In other embodiments, insulin is obtained such that it already comprises zinc when it is obtained—for example, insulin is pre-complexed with zinc.

Clioquinol is an antifungal drug that belongs to the hydroxyquinolones. Clioquinol is also a metal chelator that can chelate the excess metals found in the Alzheimer's brain and other nervous diseases. Some human studies showed improvement of memory retention and cognition. The problem with these studies is that clioquinol was given systemically and side effects were experienced. Warnings of systemic toxic side effects due to the high doses required for the treatment raised concerns, and due to its chemical characteristics including its increased hydrophilicity and aqueous insolubility, its use was limited only to the dermal and systemic administration in dermal and tablet forms respectively. Intranasal delivery, in addition to the reduction of its dose to be 10% to 20% of the effective systemic dose, circumvents its systemic toxic effects in the treatment of AD.

Copper, zinc, and iron bind with A-β protein and cause it to precipitate, and leads to the formation of the toxic senile plaque. These biometals are considered the backbone of the senile plaque which is found in high concentrations in the hippocampus, olfactory bulb, and the cerebral cortex. Biometals are the target for the present embodiment of the present composition which contains the active ingredient clioquinol (Iodochlorohydroxyquin) and DMSO. The pathogenesis of AD is closely related to the oxidative stress and B-amyloid deposition in the neocortex. Clioquinol (CQ) is a potential candidate for treating AD. Recent studies and clinical trials in animals indicated that CQ can reverse the progression of Alzheimer's, Parkinson's and Huntington's diseases.

In Alzheimer's disease patients, high levels of zinc, copper and iron in their redox active state, were detected in their serum and CSF, and were found to accumulate in the plaque of the AD brain particularly in the olfactory, hippocampus and amygdalia regions. The pathogenesis of AD is closely related to the oxidative stress and AB deposition in the neocortex. The oxidative or oxidation stress involves the generation of free radical oxygen (O2) and hydrogen peroxide (H2O2) in the presence of biometals such as zinc, copper and iron; they facilitate the aggregation and toxicity of AB.

The use of chelators as a strategy for treating and reversing AD is our strategy in developing a treatment for neurodegenerative diseases, therefore; CQ was our candidate of choice to be formulated as Drug NA-571.

Clioquinol may be present in a pharmaceutical composition of the invention at a dose of approximately 0.3 g/mL to 0.6 g/mL, preferable about 0.45 g/mL.

Glycerin, propylene glycol, polyethylene glycol, and DMSO may be used as co-solvents to maintain the aqueous solubility of clioquinol.

In certain embodiments, a pharmaceutical composition of the invention comprises sodium chloride.

In certain embodiments, a pharmaceutical composition of the invention comprises sodium hydroxide, which may be used for the adjustment of pH. Other suitable bases may be used as well. Any suitable acid, such as hydrochloric acid, may also be used to adjust pH.

The invention also includes a process to dissolve, stabilize and incorporate clioquinol into an intranasal preparation. Clioquinol dissolves in DMSO. However, it precipitates upon the addition of an aqueous vehicle to that combination. In order to dissolve in an aqueous medium clioquinol requires a pH of approximately 11. A buffering system was developed that maintains the solubility and stability of clioquinol within a pH 7-8 which is compatible with the physiological pH oh the nasal tissue. The buffering system was adjusted to provide a capacity of pH 5-7, within which the preparation will be contained within 7-8 pH. The choice of the buffering system was based on the safety, chemical and physical effects of its ingredients on clioquinol and the other ingredients incorporated in the formula, as well as its effects on the end user of present pharmaceutical composition. The buffer system comprises boric acid and sodium carbonate in certain proportions to produce a protective pH 7-8 at which clioquinol stays physically and chemically stable.

Boric acid is a weak acid of boron, and it is found in sea water, plant and in most fruits. It is soluble in water and does not dissociate in aqueous solutions. Its use in this buffer is to provide the acidic border or end of the buffer system, beyond which the clioquinol solution will start to precipitate. Sodium bicarbonate is an alkalinizing agent, it provide the alkaline border or end for the buffer system, beyond which the clioquinol will precipitate. Another effective buffering system includes sodium phosphate monobasic with sodium phosphate dibasic. Yet another effective buffering system includes sodium phosphate heptahydrate.

In certain embodiments, a pharmaceutical composition of the invention comprises boric acid. Boric acid may be present in an amount from about 0.1% (w/v) to about 0.3% (w/v), preferably about 0.13-0.21% (w/v).

In certain embodiments, a pharmaceutical composition of the invention comprises sodium bicarbonate. Sodium bicarbonate may be present in an amount from about 0.1 to about 0.3% (w/v), preferably about 0.13-0.21% (w/v).

In certain embodiments, a pharmaceutical composition of the invention comprises a buffer system of sodium phosphate monobasic and sodium phosphate dibasic.

In certain embodiments, a pharmaceutical composition of the invention comprises sodium phosphate dibasic heptahydrate as a buffer.

The pharmaceutical compositions of the invention can also be used in methods of the invention. Pre-clinical animal studies (discussed below) have demonstrated significant improvement of cognition and memory retention after the nasal administration of the present composition comprising insulin and DMSO. Further, pharmacokinetics (PK) in mice showed excellent distribution through the brain of the present composition comprising insulin and DMSO within 5 minutes after nasal administration to mice The pharmaceutical compositions of the invention may be administered to treat a neurodegenerative disorder such as Alzheimer's disease, stroke, Parkinson's disease, multiple sclerosis, spinal cord injuries, traumatic brain injuries and other nervous system and systemic diseases, in addition to local diseases. The pharmaceutical compositions may be administered to treat, prevent, or reverse cognitive decline in a human subject having clinical or pre-clinical Alzheimer's disease. The pharmaceutical compositions can combat and reverse the degenerative effects associated with AD, neurodegenerative diseases, and other nervous system diseases, systemic and local diseases. The pharmaceutical compositions may be administered to improve cognition in a human subject having clinical or pre-clinical Alzheimer's disease.

The effectiveness of the compositions of the invention for the above methods is shown by utilizing known models for neurodegenerative diseases such as Alzheimer's disease, stroke, Parkinson's disease, multiple sclerosis, spinal cord injuries, traumatic brain injuries and other nervous system and systemic diseases, in addition to local diseases. For example, an accepted model for neurodegenerative disorders such as Alzheimer's disease utilizes the senescence accelerated mouse (SAMP8). The SAMP8 mouse is a spontaneous animal model of overproduction of amyloid precursor protein (APP) and oxidative damage. It develops early memory disturbances and changes in the blood brain barrier resulting in decreased efflux of beta-amyloid protein from the brain. It has a marked increase in oxidative stress in the brain. These SAMP8 mice may be treated with the compositions of the invention and memory retention may be measured by performance in various accepted tests for memory retention such as a T-maze foot shock avoidance test, performance in an object recognition test, passive avoidance, one way active avoidance, lever press appetitive task, Greek cross, Morris Water maze, etc. See Morley et al, The senescence accelerated mouse (SAMPi) as a model for oxidative stress and Alzheimer's disease, Biochimica et Biophysica Act 1882 (2012) 650-656.

EXAMPLE 1

A composition was prepared according to the formulation in Table 1 and using the steps below.

TABLE 1

Intranasal Insulin 500 IU/mL/DMSO Formulation, quantity 5 mL (NA135)

| Ingredient | Form | Quantity | Role |
|---|---|---|---|
| Insulin (Human Recombinant) | Powder | 0.0865 g | Main active ingredient |
| DMSO 99.9% | Liquid | 1.5 mL | Active ingredient, hydrophilic/hydrophobic solvent, stabilizer, dissolves beta amyloid, and prevents its aggregation |
| Polyethylene Glycol | Liquid | 0.1 mL | Specific insulin stabilizer, co-solvent |
| Glycerin USP (Synthetic) | Liquid | 0.075 mL | Mainly co-solvent, adjusts osmalarity, preservative in higher concentrations (50%) |
| Phenol liquefied, USP/NF | Liquid | 0.005 mL | Preservative, insulin crystal stabilizer |
| Water for injection | Liquid | Quantity Sufficient to reach final volume | Main vehicle (bulk vehicle) |

Phenol and glycerin were combined in a sterile container with the required volume of sterile water.

In another container, zinc oxide was suspended in a calculated volume of water, and then treated with hydrochloric acid to produce zinc chloride.

A third container was rinsed with DMSO, then washed with normal saline to ensure that insulin was not adsorbed into the wall of the container which was used to create crystalline zinc insulin. The crystalline zinc insulin was formed by the addition of insulin powder to that container.

When the insulin was dissolved, a calculated portion of the bulk vehicle was added to the insulin and the pH was adjusted by the addition of sodium hydroxide until a pH of 4 was reached, taking into consideration that the insulin solution had a pH of 2. The calculated amount of DMSO was added to the final volume of the preparation and filtered to a third container that was previously treated with DMSO/saline solution and labeled.

The final pH of the solution may be adjusted as necessary using sodium chloride, hydrochloric acid, or any other base or acid appropriate for adjusting the pH. For instance, the pH may be adjusted to physiological pH, or, for example, pH 7-8.

The composition was subjected to stability studies. The original potency of the composition was determined at $T_0$. The composition was found to meet US Pharmacopeial potency requirements and set a baseline. The composition was then examined for potency at various increments. The results are shown below in Table 2.

TABLE 2

Results of Stability Testing on NA135

| Time | Concentration | Potency | Comments |
|---|---|---|---|
| $T_0$ | 461.25 IU/mL | 92.2% | Meets USP requirements and establishes baseline |
| 1 month | 458.45 IU/mL | 91.7% | Potency declined slightly |
| 2 months | 460.46 IU/mL | 92.1% | Potency remains steady |
| 3 months | 462.08 IU/mL | 92.4% | Potency remains steady |

These results show that the formulation was stable over a period of 3 months.

EXAMPLE 2

A composition was prepared according to the formulation in Table 3 and using the steps below.

TABLE 3

Intranasal Clioquinol 3%/DMSO Formulation, quantity 15 mL (NA571)

| Ingredient | Form | Quantity | Role |
|---|---|---|---|
| Clioquinol | Powder | 0.45 g | Main active ingredient |
| DMSO 99.9% | Liquid | 6.5 mL | Active ingredient, hydrophilic/hydrophobic solvent, stabilizer, dissolves beta amyloid, and prevents its aggregation |
| Polyethylene Glycol 400 | Liquid | 1 mL | Stabilizer and co-solvent |
| Propylene Glycol | Liquid | 1 mL | Stabilizer and co-solvent |
| Glycerin USP (Synthetic) | Liquid | 4 mL | Co-solvent, adjusts osmalarity |
| Boric acid | Powder | 0.025 g | Buffer system |
| Sodium bicarbonate | Powder | 0.045 g | Buffer system |
| NaCl 0.9% | Liquid | Quantity Sufficient to reach final volume | Diluent/co-solvent |

The weighed amount of clioquinol was placed in an empty and dry glass beaker,

The measured volumes of propylene glycol and polyethylene glycol were then added to the beaker and the beaker was placed on a stifling plate and heated to 120 C.°. Stirring continued for 10 minutes.

While stifling, ⅔ the amount of DMSO was added. Stirring was continued until the contents of the beaker were clear. The heat was turned off and stirring was continued until cooled.

The weighed amounts of boric acid and sodium bicarbonate where added into a second beaker. The measured volumes of sodium chloride and glycerin were also added. The solution was stirred until clear.

The contents of the second beaker were added to the contents of the first beaker with stirring. The contents in the beaker turned into a grayish green suspension. Stirring was continued for 5 minutes to ensure homogeneous mixing.

The pH of the suspension was adjusted to 7-8 using sodium hydroxide 10% solution drop wise until the suspension turned completely clear. The final pH was 7-8.

In the foregoing example, sodium phosphate monobasic and sodium phosphate dibasic may be used in the buffering system in place of boric acid and sodium bicarbonate. For instance, 0.135 g sodium phosphate monobasic and 0.015 g sodium phosphate dibasic may be used rather than boric acid and sodium bicarbonate. Alternatively, 0.145 g sodium phosphate dibasic heptahydrate may be used as a buffering agent rather than boric acid and sodium bicarbonate.

The composition shown in Table 3 was subjected to stability studies. The original potency of the composition was determined at $T_0$. The composition was found to meet US Pharmacopeial potency requirements and set a baseline. The composition was then examined for potency at various increments. The results are shown below in Table 4.

TABLE 4

Results of Stability Testing on NA571

| Time | Concentration | Potency | Comments |
|---|---|---|---|
| $T_0$ | 3.15% | 105.0% | Meets USP requirements and establishes baseline |
| 1 month | 3.14% | 104.6% | Sample remains stable |
| 2 months | 3.13% | 104.3% | Sample remains stable |
| 3 months | 2.99% | 99.7% | Sample declining but still good |

These results show that the formulation was stable over a period of 3 months.

EXAMPLE 3

A composition was prepared according to the formulation in Table 5 and using the steps below.

TABLE 5

Intranasal Clioquinol 3%/Insulin 500 IU/mL/DMSO Formulation, quantity 15 mL (NA753)

| Ingredient | Form | Quantity | Role |
|---|---|---|---|
| Insulin (Human Recombinant) | Powder | 0.312 g | Main active ingredient |
| Clioquinol | Powder | 0.45 g | Main active ingredient |
| DMSO 99.9% | Liquid | 6.5 mL | Active ingredient, hydrophilic/hydrophobic solvent, stabilizer, dissolves beta amyloid, and prevents its aggregation |
| Polyethylene Glycol 400 | Liquid | 1 mL | Stabilizer and co-solvent |
| Propylene Glycol | Liquid | 1 mL | Stabilizer and co-solvent |
| Glycerin USP (Synthetic) | Liquid | 4 mL | Co-solvent |
| Phenol liquefied, USP/NF | Liquid | 0.015 mL | Co-stabilizer and preservative |
| Boric acid | Powder | 0.025 g | Buffer system |
| Sodium bicarbonate | Powder | 0.045 g | Buffer system |
| NaCl 0.9% | Liquid | Quantity Sufficient to reach final volume | Diluent/co-solvent |

The weighed amount of clioquinol was placed in an empty and dry glass beaker,

The measured volumes of propylene glycol and polyethylene glycol were then added to the beaker and the beaker was placed on a stifling plate and heated to 120 C.°. Stirring continued for 10 minutes.

While stirring, ⅔ the amount of DMSO was added. Stirring was continued until the contents of the beaker were clear. The heat was turned off and stirring was continued until cooled.

The weighed amounts of boric acid and sodium bicarbonate where added into a second beaker. The measured volumes of sodium chloride and glycerin were also added. The solution was stirred until clear.

The contents of the second beaker were added to the contents of the first beaker with stirring. The contents in the beaker turned into a grayish green suspension. Stifling was continued for 5 minutes to ensure homogeneous mixing.

The pH of the suspension was adjusted to 7-8 using sodium hydroxide 10% solution drop wise until the suspension turned completely clear. The final pH was 7-8.

A clear vial was rinsed with 0.5 mL DMSO and dried. The insulin was prepared by placing ⅓ of the DMSO in the vial and adding the insulin powder. Then mixing gently until clear. A warm water bath was used to speed the dissolution of the insulin in DMSO.

Hydrochloric acid 0.1 normal was used dropwise to completely clear the insulin solution.

The insulin was added to the beaker containing the clear clioquinol solution while slowly stirring. The solution became cloudy again.

Stirring was continued while adding 10% sodium hydroxide until a clear solution was obtained.

In the foregoing example, sodium phosphate monobasic and sodium phosphate dibasic may be used in the buffering system in place of boric acid and sodium bicarbonate. For instance, 0.135 g sodium phosphate monobasic and 0.015 g sodium phosphate dibasic may be used rather than boric acid and sodium bicarbonate. Alternatively, 0.025 g sodium phosphate dibasic heptahydrate may be used as a buffering agent rather than boric acid and sodium bicarbonate.

The composition was then subjected to stability studies. The original potency of the composition was determined at $T_0$. The composition was found to meet US Pharmacopeial potency requirements and set a baseline. The composition was then examined for potency at various increments. The results are shown below in Table 6.

TABLE 6

Results of Stability Testing on NA753

| Time | Concentration | Potency | Comments |
| --- | --- | --- | --- |
| $T_0$ | Insulin 527 IU/mL | 105.4% | Meets USP requirements and establishes baseline |
|  | Clioquinol 2.82% | 94.0% |  |

These results show that the formulation was stable when produced.

EXAMPLE 4

Figure 1:
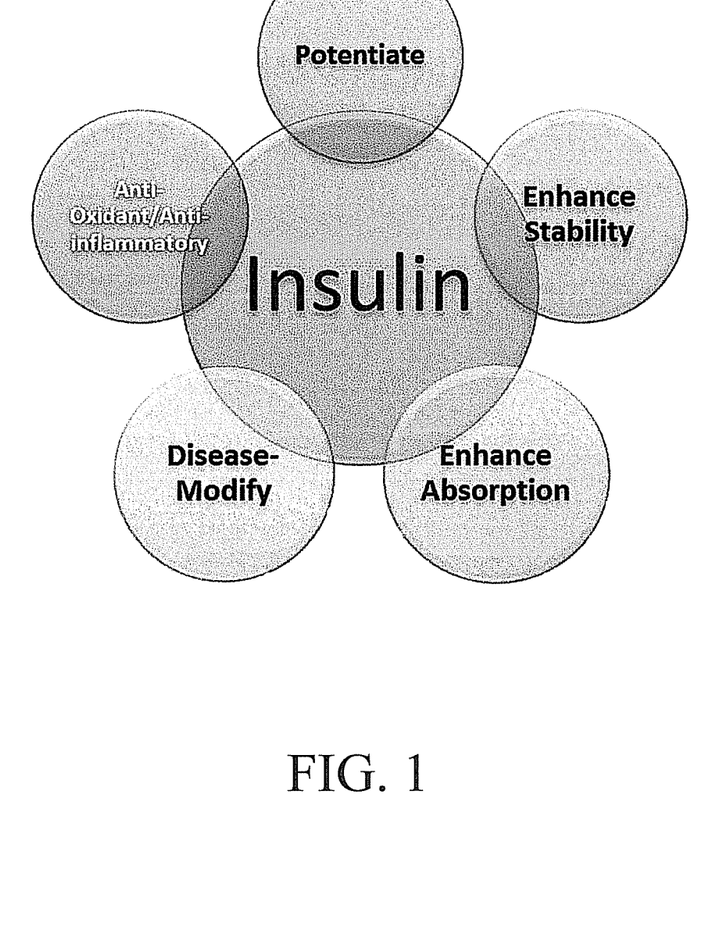
FIG. 1 shows the pharmacological actions of excipients in NA135.
Figure 2:
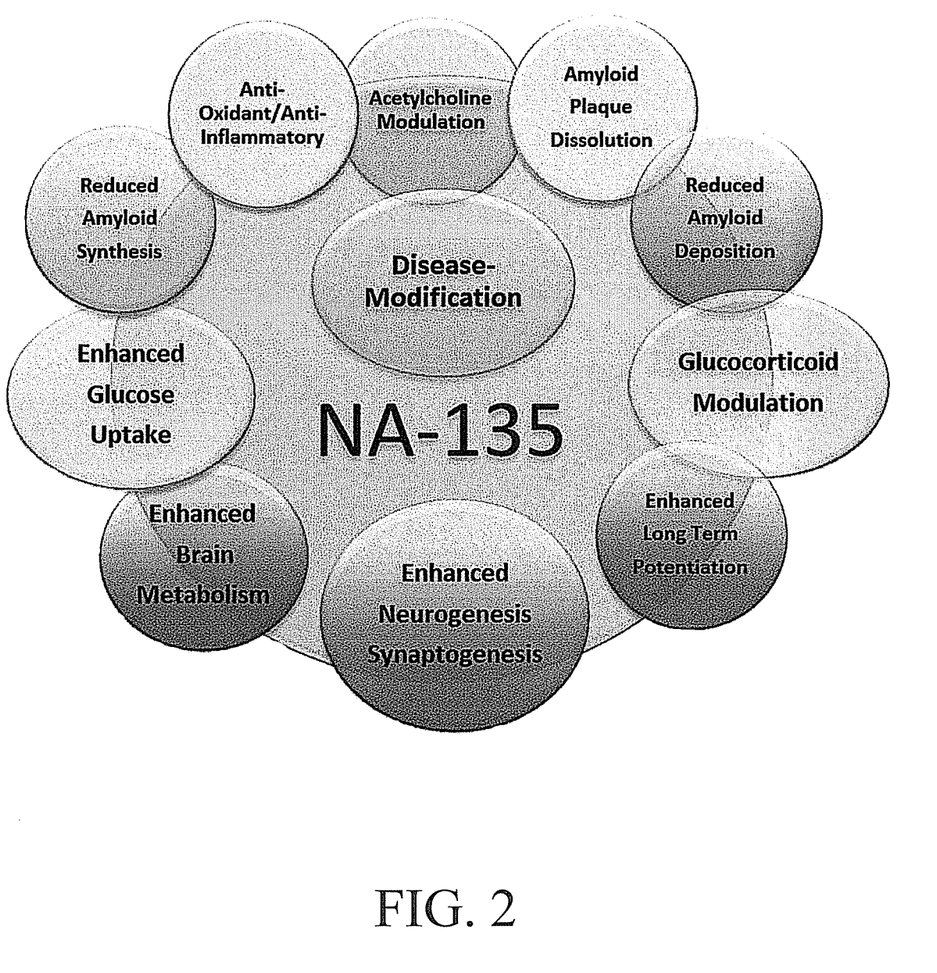
FIG. 2 shows the overall pharmacological actions of NA135.
Figure 3:
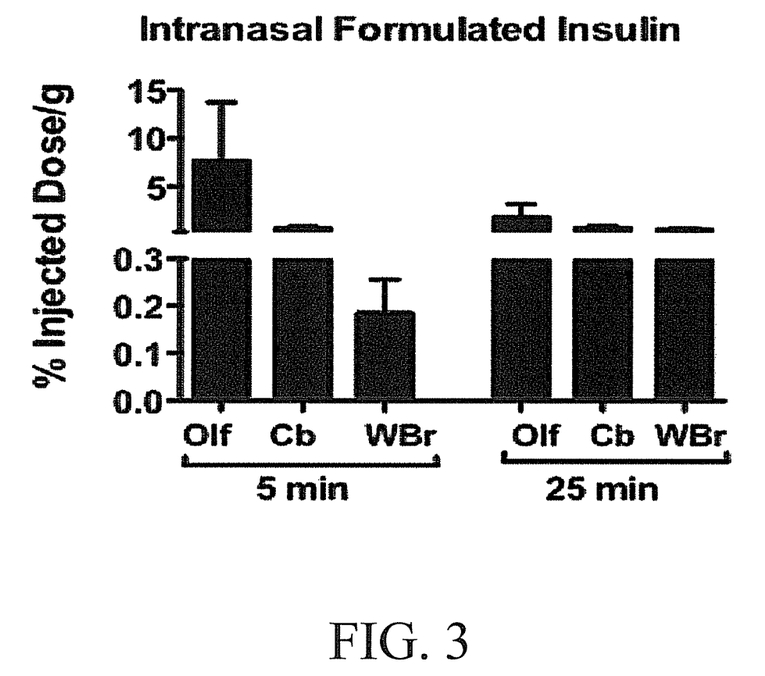
FIG. 3 shows results of brain dissection of mice after administration of a radiolabelled version of one embodiment of the pharmaceutical composition of the invention. Specifically, the figure shows results from brain dissection of mice after administration of a radiolabelled version of NA135 in percent of the injected dose per gram 5 minutes and 25 minutes after injection. "Olf" is olfactory bulb; "Cb" is cerebellum; and "WBr" is whole brain—referring to the amount of radiolabelled insulin found in each anatomical structure.

The composition of Example 1 was radioactively labeled and administered intranasally to 10 mice. Five mice were sacrificed at 5 minutes and 5 at 25 minutes. The brains of the mice were removed and the radioactively labeled insulin in the olfactory bulb, cerebellum and whole brain of the mice was measured. The percent of the injected dose per gram of brain matter (% injected dose/g) was measured. The results are shown in FIG. 3 and Table 7.

TABLE 7

Results of Brain Dissection of Mice after Administration of Intranasal Insulin 500 IU/mL/DMSO Formulation (% injected dose/g)

|  | Minimum | Maximum | Mean | Std. Deviation | Std. Error |
| --- | --- | --- | --- | --- | --- |
| 5 min olfactory bulb | 0.1302 | 31.83 | 7.658 | 13.60 | 6.083 |
| 5 min cerebellum | 0.0 | 1.301 | 0.6063 | 0.5544 | 0.2479 |
| 5 min whole brain | 0.02372 | 0.3893 | 0.1845 | 0.1608 | 0.07190 |
| 25 min olfactory bulb | 0.0 | 7.360 | 1.823 | 3.117 | 1.394 |
| 25 min cerebellum | 0.0 | 1.484 | 0.7196 | 0.5371 | 0.2402 |
| 25 min whole brain | 0.2266 | 0.7924 | 0.5422 | 0.2032 | 0.09086 |

The fact that the mean values for the % injected dose per gram are not zero shows that the composition of Example 1 was absorbed in the olfactory bulb, cerebellum and whole brain. The increase in the mean values for the % injected dose per gram for the whole brain show that the composition is absorbing into the whole brain over time. The steady mean values for the % injected dose per gram in the cerebellum shows good cerebrospinal fluid (CSF) diffusion.

EXAMPLE 5

The composition of Example 1 was utilized in a neurodegenerative disorder model with SAMP8 mice in the T-maze foot shock test or object recognition test.

Twelve-month old SAMP8 mice were trained in either T-maze foot shock avoidance or object recognition. In the T-maze, mice were trained until they learned to avoid the shock one time. Immediately after training, mice were administered the composition form Example 1 intranasally. The composition was administered at 0, 0.01 or 0.1 IU/0.1 uL doses for one week.

One week later mice were returned to the maze and training was continued until they made 5 avoidances in 6 consecutive trials. The number of trials to make criterion is the measure of retention. The fewer trials to reach criterion, the better the retention.

In object recognition, after three 5 minute habituation sessions with no objects, mice were placed in the apparatus with 2 identical objects for 5 minutes and allowed to explore the objects. Immediately after the 5 minute exposure mice were administered the composition of Example 1 intranasally. The composition was administered at 0 or 0.1 IU/1 ul).

Twenty four hours later mice were place in the apparatus for 5 minutes with 1 object from the initial exposure and one new object for 5 minutes. The amount of time exploring the two objects was recorded. The percentage of time exploring the novel object is the measure of retention. The greater time spent exploring the novel object the better the retention.

Figure 4:
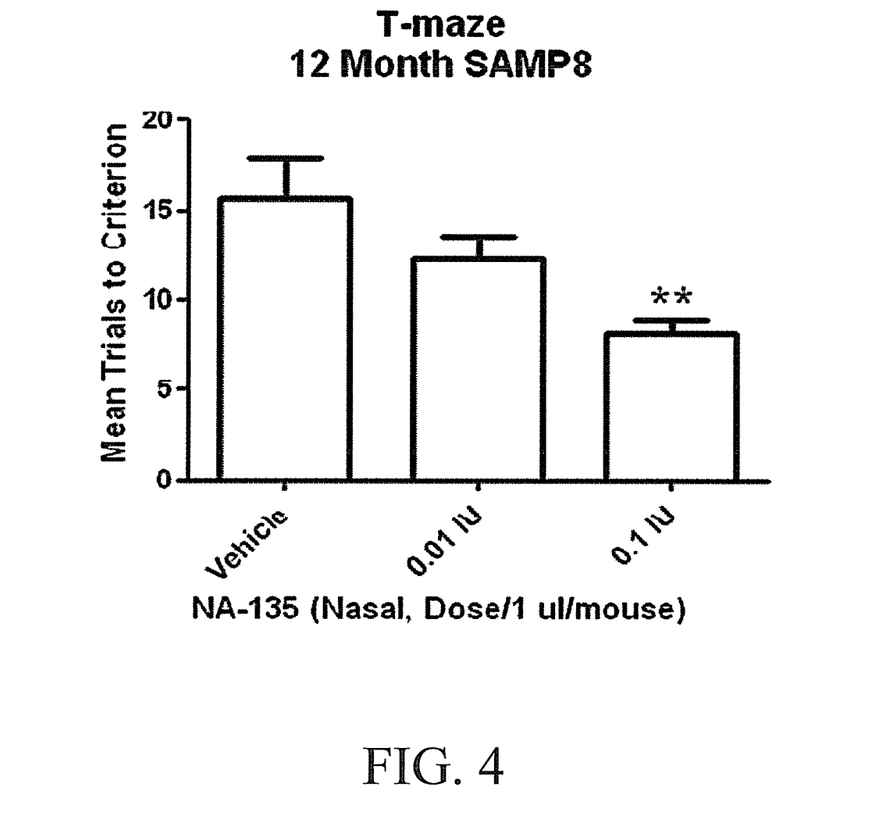
FIG. 4 shows results of memory retention tests on SAMP8 mice in the T-maze foot shock test after administration of one embodiment of the pharmaceutical composition of the invention. Specifically, the figure shows results from memory retention tests on SAMP8 mice in the T-maze foot shock test after administration of NA135.

The results of the T-maze foot shock test are shown in FIG. 4. FIG. 4 shows that the animals that received none of the composition of Example 1 required more trials to make criterion (~15) than those who received 0.01 UL (~12) or 0.1 UL (~8). This indicates that those mice that received the composition of Example 1 had improved cognition.

Figure 5:
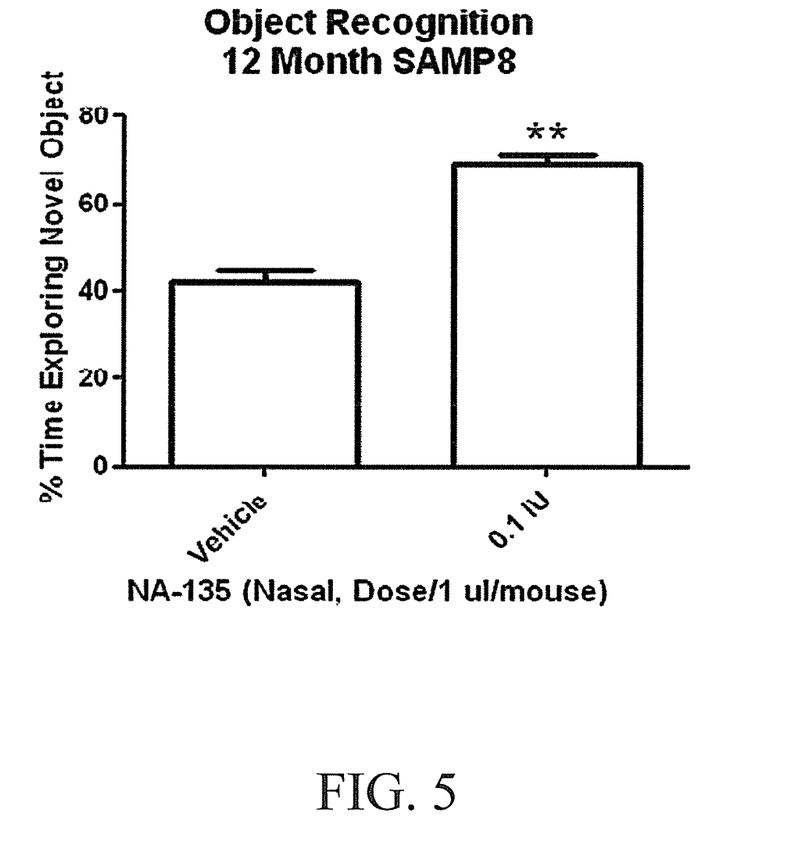
FIG. 5 shows results of memory retention tests on SAMP8 mice in the object recognition test after administration of one embodiment of the pharmaceutical composition of the invention. Specifically, the figure shows results from memory retention tests on SAMP8 mice in the object recognition test after administration of NA135.
Figure 6:
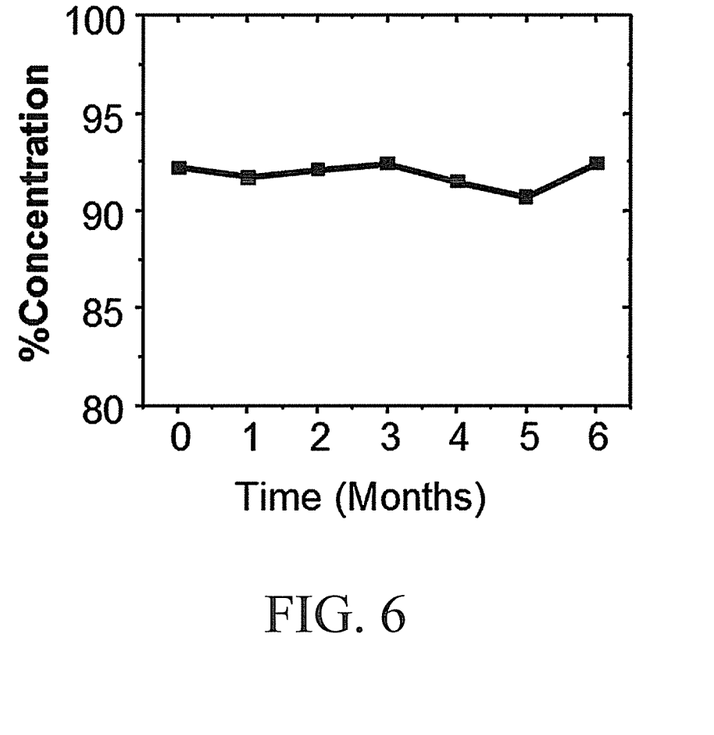
FIG. 6 shows results of stability testing of NA135. Specifically, the figure shows the percent concentration of insulin remaining in the composition up to six months after formulation of the composition.

The results of the object recognition test are shown in FIG. 5. FIG. 5 shows that the animals that received none of the composition of Example 1 spent a smaller amount of time exploring the novel object (~40%) than those who received 0.1 UL (~65%). This indicates that those mice that received the composition of Example 1 had improved cognition.

EXAMPLE 6

A composition was prepared according to the formulation in Table 8 and using the steps below.

TABLE 8

Intranasal Insulin 5000 IU/mL/DMSO Formulation, quantity 5 mL

| Ingredient | Form | Quantity | Role |
|---|---|---|---|
| Insulin (Human Recombinant) | Powder | 1.04 g | Main active ingredient |
| DMSO 99.9% | Liquid | 2.00 mL | Active ingredient, hydrophilic/hydrophobic solvent, stabilizer, dissolves beta amyloid, and prevents its aggregation |
| Polyethylene Glycol | Liquid | 0.20 mL | Specific insulin stabilizer, co-solvent |
| Glycerin USP (Synthetic) | Liquid | 0.15 mL | Mainly co-solvent, adjusts osmalarity, preservative in higher concentrations (50%) |
| Phenol liquefied, USP/NF | Liquid | 0.0375 mL | Preservative, insulin crystal stabilizer |
| Water | Liquid | Quantity Sufficient to reach final volume | Main vehicle (bulk vehicle) |

In a vial rinsed with DMSO and left to dry, add the calculated amount of DMSO followed by insulin powder. Shake gently for 10 minutes until it is clear.

Add the polyethylene glycol followed by glycerin and phenol and continue mixing. Add the water for injection in a quantity sufficient to 5 ml. HCL 0.1 normal might be added dropwise to adjust the pH to 4-4.5.

The composition was then subjected to stability studies. The original potency of the composition was determined at $T_0$. The composition was found to meet US Pharmacopeial potency requirements and set a baseline. The composition was then examined for potency at various increments. The results are shown below in Table 9.

TABLE 9

Results of Stability Testing on Intranasal Insulin 5000 IU/mL/DMSO Formulation

| Time | Concentration | Potency | Comments |
|---|---|---|---|
| $T_0$ | 5237 IU/mL | 104.7% | Meets USP requirements and establishes baseline |
| 1 month | 5129 IU/mL | 102.6% | Remains stable |
| 2 months | 5133 IU/mL | 102.7% | Remains stable |
| 3 months | 5050 IU/mL | 101.0% | Potency declining but sample remains stable |
| 4 months | 5019 IU/mL | 100.4% | Remains stable |

These results show that the formulation was stable over a period of 4 months. This formulation is appropriate for FDA toxicity studies.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to any particular embodiment disclosed.

The invention claimed is:

1. A pharmaceutical composition for intranasal administration consisting of:
   insulin present in an amount from about 400 IU/mL to about 600 IU/mL;
   dimethyl sulfoxide present in an amount from about 24% (v/v) to about 36% (v/v);
   polyethylene glycol present in an amount from about 1.6% (v/v) to about 2.4% (v/v);
   glycerin present in an amount from about 1.2% (v/v) to about 1.8% (v/v);
   phenol present in an amount from about 0.05% (v/v) to about 0.15% (v/v);
   and water in a quantity sufficient to reach final volume.

2. The composition of claim 1, consisting of about 500 IU/mL insulin, about 30% (v/v) dimethyl sulfoxide, about 2% (v/v) polyethylene glycol, about 1.5% (v/v) glycerin, about 0.1% (v/v) phenol; and water in a quantity sufficient to reach final volume.

3. A method of treating a neurodegenerative disorder in a patient, comprising intranasally administering the composition of claim 1 to the patient.

* * * * *